(12) United States Patent
Chatillon et al.

(10) Patent No.: US 12,558,574 B2
(45) Date of Patent: Feb. 24, 2026

(54) METHOD AND SYSTEM FOR PARAMETERISING A HIGH-INTENSITY FOCUSED ULTRASOUND TREATMENT DEVICE

(71) Applicants: COMMISSARIAT A L'ENERGIE ATOMIQUE ET AUX ENERGIES ALTERNATIVES, Paris (FR); EDAP-TMS, Vaulx en Velin (FR)

(72) Inventors: Sylvain Chatillon, Palaiseau (FR); Michel Cardoso, Boulogne-Billancourt (FR); Nicolas Guillen, Fontaines sur Saone (FR)

(73) Assignees: COMMISSARIAT A L'ENERGIE ATOMIQUE ET AUX ENERGIES ALTERNATIVES, Paris (FR); EDAP-TMS, Vaulx en Velin (FR)

( * ) Notice: Subject to any disclaimer, the term of this patent is extended or adjusted under 35 U.S.C. 154(b) by 0 days.

(21) Appl. No.: 18/718,286

(22) PCT Filed: Dec. 16, 2022

(86) PCT No.: PCT/FR2022/052404
§ 371 (c)(1),
(2) Date: Jun. 10, 2024

(87) PCT Pub. No.: WO2023/111487
PCT Pub. Date: Jun. 22, 2023

(65) Prior Publication Data
US 2025/0108236 A1 Apr. 3, 2025

(30) Foreign Application Priority Data
Dec. 17, 2021 (FR) ...................................... 2113901

(51) Int. Cl.
*A61N 7/02* (2006.01)

(52) U.S. Cl.
CPC ...................................... *A61N 7/02* (2013.01)

(58) Field of Classification Search
CPC ...................................... A61N 7/02
See application file for complete search history.

(56) References Cited

U.S. PATENT DOCUMENTS

| | | | |
|---|---|---|---|
| 2004/0030227 A1* | 2/2004 | Littrup | A61N 7/02 |
| | | | 600/300 |
| 2012/0123400 A1* | 5/2012 | Francischelli | A61B 18/12 |
| | | | 606/41 |

(Continued)

FOREIGN PATENT DOCUMENTS

WO WO 2019/053614 A1 3/2019

OTHER PUBLICATIONS

International Search Report issued Mar. 28, 2023 in PCT/FR2022/052404, filed on Dec. 16, 2022, 3 pages.

(Continued)

*Primary Examiner* — Hien N Nguyen
(74) *Attorney, Agent, or Firm* — Oblon, McClelland, Maier & Neustadt, L.L.P.

(57) ABSTRACT

A parameterising method and system integrated within a high-intensity focused ultrasound (HIFU) treatment device. The parameterising system includes a real-time simulation unit that makes it possible to predict, on the basis of geometric and physiological parameters of tissue regions in the area to be treated, and treatment parameters, the distribution of the ultrasonic field within the area. The computation is performed in real time by means of a metamodel: the ultrasonic field is estimated from an interpolation of maps of the ultrasonic field which are pre-computed and stored in a database, the maps being associated with different values of the geometric and physiological parameters of the tissue regions in question. The thermal dose applied at each point during treatment is subsequently computed and the tissue (Continued)

response is estimated. It is possible for the practitioner to check at any time that the simulated treatment is being used in accordance with tissue regions to be necrotised and tissue regions to be spared. The treatment parameters can be iteratively adjusted in order to conform to the objective.

13 Claims, 4 Drawing Sheets

(56) References Cited

U.S. PATENT DOCUMENTS

| | | | |
|---|---|---|---|
| 2014/0296842 A1 | 10/2014 | Mansi et al. | |
| 2015/0142034 A1* | 5/2015 | Kohler | A61N 7/02 |
| | | | 606/169 |
| 2015/0273245 A1* | 10/2015 | Nurmilaukas | A61N 7/02 |
| | | | 601/3 |
| 2016/0029998 A1* | 2/2016 | Brister | A61B 8/0833 |
| | | | 600/424 |
| 2021/0000541 A1 | 1/2021 | Levy et al. | |

OTHER PUBLICATIONS

French Preliminary Search Report issued Oct. 24, 2022 in FR 2113901 filed on Dec. 17, 2021, 12 pages (with English Translation of Cited Documents and Written Opinion).

Chatillon et al., "Applications of intensive HIFU simulation based on surrogate models using the CIVA HealthCare platform", Journal of Physics: Conference Series, Institute of Physics Publishing, Bristol, GB, vol. 1761, No. 1, 2021, 11 pages.

French Preliminary Search Report and Written Opinion issued Oct. 24, 2022, 12 pages.

Sapareto SA et al.: "Thermal dose determination in cancer therapy", International Journal of Radiation: Oncology Biology Physics, Pergamon Press, USA, vol. 10, No. 6, Apr. 1, 1984 (Apr. 1, 1984), pp. 787-800.

Liu Xilun et al.: "An Optimized Control Approach for HIFU Tissue Ablation Using PDE Constrained Optimization Method", IEEE Transactions on Ultrasonics, Ferroelectrics, and Frequency Control, IEEE, USA, vol. 68, No. 5, Nov. 25, 2020 (Nov. 25, 2020), pp. 1555-1568.

* cited by examiner

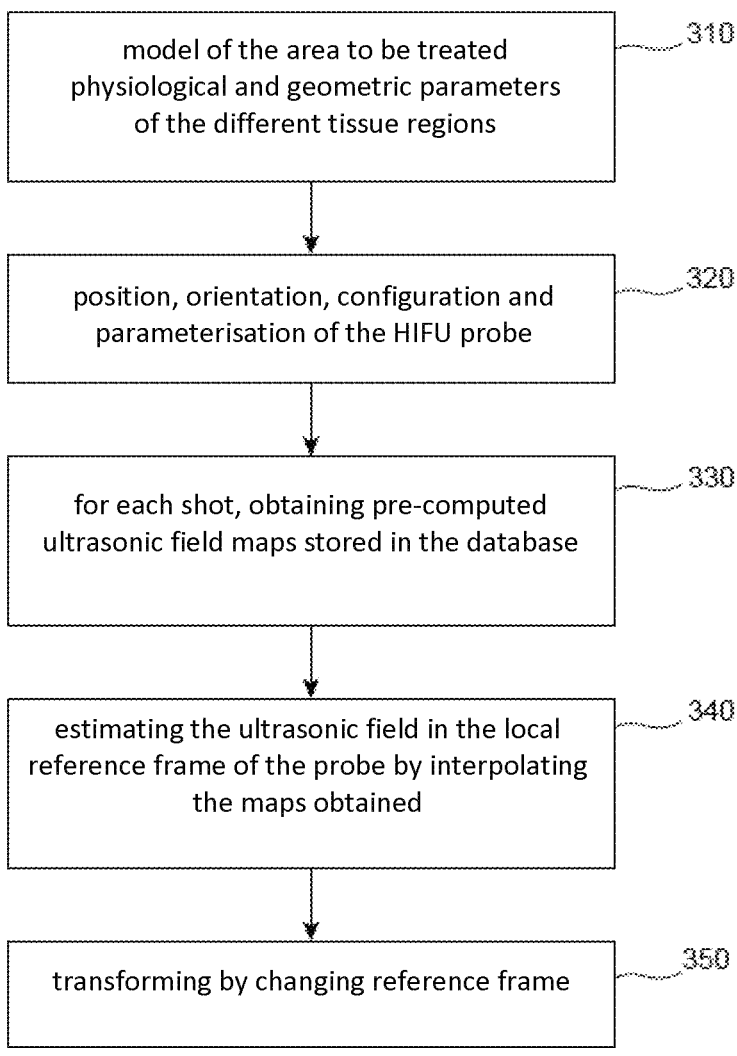

model of the area to be treated
physiological and geometric parameters
of the different tissue regions ⟋310 position, orientation, configuration and
parameterisation of the HIFU probe ⟋320 for each shot, obtaining pre-computed
ultrasonic field maps stored in the database ⟋330 estimating the ultrasonic field in the local
reference frame of the probe by interpolating
the maps obtained ⟋340 transforming by changing reference frame ⟋350

Fig. 3

METHOD AND SYSTEM FOR PARAMETERISING A HIGH-INTENSITY FOCUSED ULTRASOUND TREATMENT DEVICE

TECHNICAL FIELD

The present invention relates generally to treatment devices using High-Intensity Focused Ultrasound (HIFU). In particular, it is used for tumour destruction by remote thermal ablation with preservation of intermediate tissues.

PRIOR ART

High-intensity focused ultrasound (HIFU) therapy involves using the energy of a focused ultrasonic beam to modify or destroy biological tissue. Tissue is destroyed by protein coagulation, leading to irreversible cell damage and apoptosis.

This technique is widely used for the thermal ablation of benign or malignant tumours (prostate cancer, liver metastases, or brain tumours). It has the advantage of being percutaneous (i.e. non-invasive) and of preserving the surrounding healthy tissue.

HIFU treatment generally uses a phased array multi-transducer probe. For each ultrasound shot, a delay law and an amplitude law are applied to the various elements of the transducer, so as to form a focused beam at a predetermined point. The operation is repeated at different points in the target area to be destroyed, with a choice of repetition rate (recurrence frequency) and pulse energy.

Before applying the treatment protocol, the practitioner must ensure that the thermal dose applied is sufficient to destroy the target area while preserving healthy areas. To do this, the target area is meshed by a grid of points and a simulation of focused ultrasound shots is carried out at each point or a group of adjacent points on the grid. The temperature rise at each point is then deduced by solving the heat transfer equation in the tissue. One method for validating a HIFU treatment protocol has been described in the patent application US-A-2021/0000541.

This simulation method works relatively well when the medium in which the ultrasound waves propagate is homogeneous, but becomes much more complex when several tissue areas need to be modelled, especially when high spatial resolution is required. Simulating the ultrasonic field based on the characteristics of the patient's various tissues can thus take several hours on a conventional personal computer, which is incompatible with outpatient treatment.

It has also been proposed to significantly speed up the simulation of a HIFU treatment by using a metamodel generated from a simulated database. This is obtained by defining a set of N uncertain parameters, in this case the physiological and anatomical parameters of the patient that are influential for the simulation, as well as their assumed range of variation. The database is obtained by carrying out once and for all (offline) the simulation of the ultrasonic field for all the possible configurations in this space of dimension N (basic configurations). This first simulation gives the ultrasonic pressure field distribution for each basic configuration.

A second simulation is then carried out (online) by interpolating the simulation results obtained for the various previous configurations, i.e. by interpolating the ultrasonic pressure fields contained in the database. This is referred to as a metamodel, since it involves replacing the direct simulation model, which is assumed to be accurate, with a much faster, even real-time interpolator, the error of which we can control.

Such a method for simulating a HIFU ultrasonic field was described in the article by S. Chatillon et al. entitled "Applications of intensive HIFU simulation based on surrogate models using the CIVA HealthCare platform" published in J. of Phys. 1761, 2021.

If the patient's physiological and anatomical parameters are perfectly well known, this simulation method makes it possible to estimate the lesion produced for an established protocol, and thus to check that it complies with the restrictions imposed in terms of the target area to be destroyed and the healthy tissue to be preserved. If the treatment protocol envisaged by the practitioner does not comply with the aforementioned restrictions, the practitioner must modify it empirically and carry out a new online simulation. Convergence of the process can be relatively slow and lead to a sub-optimal solution.

The aim of the present invention is therefore to propose a parameterising method and system embedded in a HIFU treatment device which does not have the above-mentioned drawbacks, and in particular which allows for quasi-optimal parameterisation very quickly on the basis of the patient's physiological parameters, the target area to be necrotised and the healthy areas to be spared.

DISCLOSURE OF THE INVENTION

The present invention is defined by a method for parameterising a HIFU treatment device equipped with an ultrasound probe for necrotising at least one tissue region of an area to be treated of a patient, said treatment being original in that it comprises a plurality of ultrasound shots and being original in that the treatment parameters define in particular the position and orientation of the probe at each shot relative to the area to be treated, the area to be treated being modelled by different tissue regions, including at least one tissue region to be necrotised and one tissue region to be preserved, each tissue region being characterised by geometric parameters and physiological parameters, said parameterisation method comprising:

a step of estimating the ultrasonic field in the area to be treated by means of a metamodel using a database in which precomputed ultrasonic field maps are stored for different values of the geometric and physiological parameters of each tissue region of said area, the ultrasonic field estimate being obtained by interpolation of precomputed maps;

a step of estimating the thermal dose applied at each point on a grid within the area to be treated from the ultrasonic field in this area;

a step of estimating the tissue response at each point on said grid to determine whether or not the thermal dose applied leads to necrosis at this point, thus defining an estimated necrotised region and an estimated preserved region;

a step of adjusting the treatment parameters in order to minimise a cost function that is dependent on the difference between the estimated necrotised region and the tissue region to be necrotised, with the condition that the region to be preserved lies within the estimated preserved region.

Said treatment parameters can also include the duration and repetition rate of the ultrasound shots.

When the probe comprises a plurality of transducers, said treatment parameters can comprise a phase and/or frequency and/or power law to be applied to all of the transducer elements.

The physiological parameters of a tissue region include, for example, at least one parameter of density, specific heat, tissue thermal conductivity, specific heat of blood or tissue blood perfusion rate.

The ultrasonic field can be estimated in the local reference frame of the probe by interpolating said pre-computed maps, the distribution of the ultrasonic field in the area to be computed being deduced by changing the reference frame.

The thermal dose is advantageously estimated by solving a heat transfer equation in the different tissue regions, taking into account the ultrasound energy absorbed at each point on the grid during each ultrasound shot.

The result of the treatment can be simulated by computing, at each point on the grid, the thermal dose absorbed at that point in the form of an exposure time equivalent to a reference temperature, the tissue being considered necrotised at that point if that time exceeds a predetermined threshold value, and preserved otherwise.

According to an alternative embodiment, the cost function depends on the difference between the extent of the tissue region to be necrotised and the extent of the estimated necrotised tissue region.

The cost function can be defined in different ways.

According to an alternative embodiment, the cost function is defined as a sum of unit cost functions associated with each of the shots.

According to certain alternative embodiments, the cost function includes a sum of a plurality of unit cost functions, each of said unit cost functions being associated with a shot, with a tissue region to be necrotised, or with a sub-region of a tissue region to be necrotised, and/or being a function intended to minimise or maximise at least one objective chosen from among a difference between a region or sub-region thereof estimated to have been necrotised by one or more shots and the corresponding region or sub-region thereof to be necrotised, a volume of healthy tissue necrotised after one or more shots, an overall duration of one or more shots, a number of positions of the probe for carrying out a set of shots, in particular all of the shots, a rest period between two consecutive shots or a sum of such rest periods.

In this sum, one or more unit cost functions can also be one or more functions resulting from all of the shots provided for by the treatment, thus aiming in particular to cover all of the one or more tissue regions to be necrotised.

A sub-region of a tissue region to be necrotised is a part of this region.

When unit cost functions are respectively associated with different shots, preferably these different shots are directed at different sub-regions of the tissue region to be necrotised.

When a unit cost function is associated with a sub-region of the region to be necrotised, one (single) shot or a plurality of shots can be provided for the sub-region in question.

In certain alternative embodiments, each of the unit cost functions is associated respectively with one of the different shots, the different shots preferably being directed at distinct sub-regions of the region to be necrotised.

In certain alternative embodiments, each of the unit cost functions is associated respectively with a sub-region of the region to be necrotised, with one shot or a plurality of shots being provided for each sub-region of the region to be necrotised.

Moreover, in certain alternative embodiments, the cost function is defined by a sum of unit cost functions, each of the unit cost functions aiming to minimise at least one objective to be minimised chosen from among the objectives indicated above.

According to certain alternative embodiments, the treatment parameters are adjusted iteratively using gradient descent, stochastic gradient descent or a genetic algorithm.

For at least one treatment parameter adjustment iteration, the estimated necrotised tissue region and/or the estimated preserved tissue region is/are advantageously displayed on a display with the tissue region to be necrotised and/or the tissue region to be preserved overlaying the image of the area to be treated.

The present invention further relates to a system for parameterising a HIFU treatment device equipped with an ultrasound probe for necrotising at least one tissue region of an area to be treated of a patient, said treatment comprising a plurality of ultrasound shots and being characterised by treatment parameters defining in particular the position and orientation of the probe at each shot relative to the area to be treated, the area to be treated being modelled by different tissue regions, including at least one tissue region to be necrotised and one tissue region to be preserved, each tissue region being characterised by geometric and physiological parameters, said parameterisation system comprising:

a module for estimating the ultrasonic field in the area to be treated by means of a metamodel, a database in which precomputed ultrasonic field maps are stored for different values of the geometric and physiological parameters of each tissue region of said area, said estimation module estimating the ultrasonic field by interpolation of precomputed maps extracted from the database;

a module for estimating the thermal dose applied at each point on a grid within the area to be treated from the ultrasonic field in this area;

a module for estimating the tissue response at each point on said grid to determine whether or not the thermal dose applied leads to necrosis at this point, thus defining an estimated necrotised region and an estimated preserved region;

a module for adjusting the treatment parameters in order to minimise a cost function that is dependent on the difference between the estimated necrotised region and the tissue region to be necrotised, with the condition that the region to be preserved lies within the estimated preserved region.

Said treatment parameters further comprise the duration and repetition rate of the ultrasound shots.

When the probe comprises a plurality of transducers, said treatment parameters can comprise a phase and/or frequency and/or power law to be applied to all of the transducer elements.

BRIEF DESCRIPTION OF THE DRAWINGS

Other features and advantages of the invention will appear upon reading a preferred embodiment of the invention, made with reference to the appended figures wherein:

FIG. 3 diagrammatically shows a method for predicting the distribution of the ultrasonic field intensity used in FIG. 2;

DETAILED DISCLOSURE OF PARTICULAR EMBODIMENTS

The description below will refer to a high-intensity focused ultrasound treatment device as described in the introduction. Such a device can be equipped with a single piezoelectric transducer probe whose shape gives the focusing law, or more generally a multi-transducer probe, the focusing law being given by the distribution of acoustic powers and delays relative to the various piezoelectric elements. In the description below, it will be assumed, for the sake of illustration and without prejudice to generalisation, that the probe is a multi-transducer probe. Treatment is carried out by successive shots, each shot corresponding to the application of a given distribution of phases, amplitudes or frequencies. The presence of heterogeneous media between the transducer and the target area can lead to the application of a specific phase, amplitude or frequency value to each transducer element. For example, absorption by a medium with high acoustic attenuation (for example an organ or a tumour) can be compensated for by increasing the power of certain transducer elements or by reducing the transmission frequency, so as to balance the energy contributions at the focal point.

The present invention is based on providing a plug-in module that can be added to or integrated into a HIFU treatment device in order to parameterise the ultrasound probe for a given area to be treated.

More specifically, the practitioner firstly defines an area to be treated in the patient's body, this area comprising parts to be necrotised (cancerous tissue, metastases, etc.) by a thermal effect (raising the local temperature to a predetermined threshold value for a given period of time) and parts to be preserved (healthy tissue).

Figure 1:
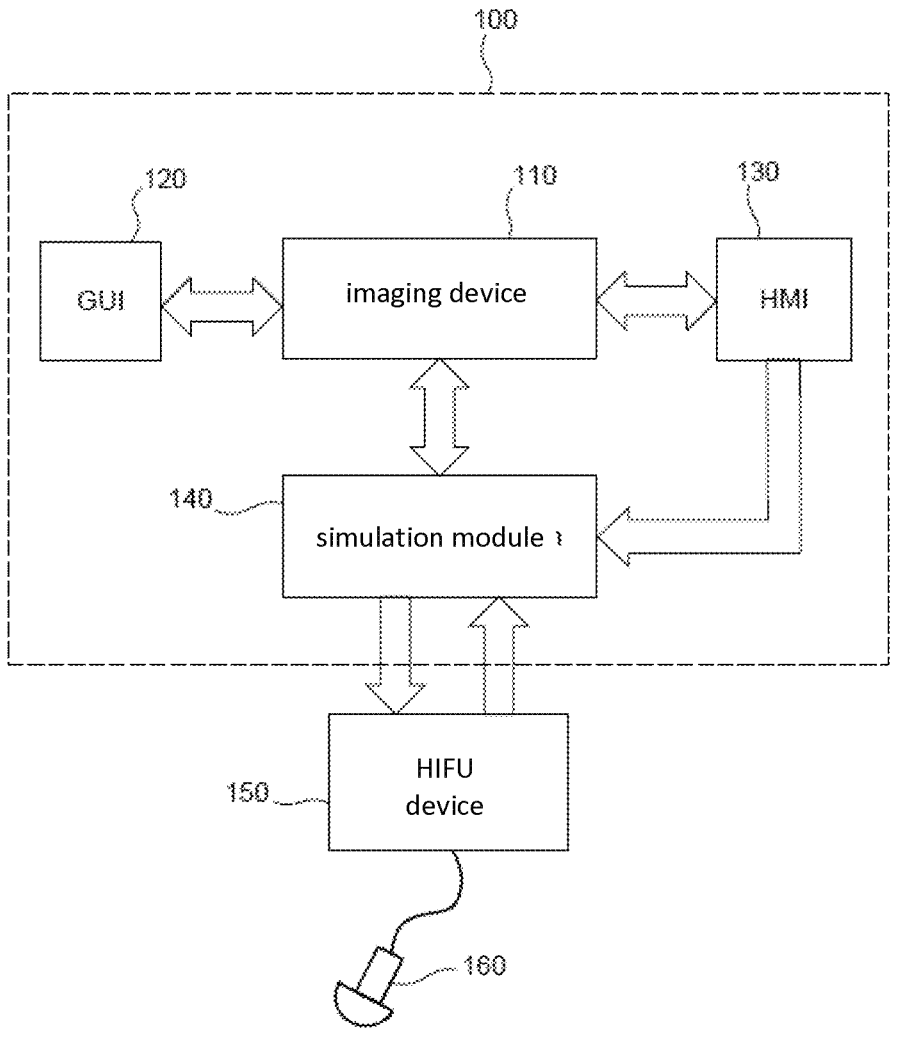
FIG. 1 diagrammatically shows a system for parameterising a HIFU treatment device according to one embodiment of the invention.

A HIFU treatment device associated with a parameterisation system according to the present invention is shown diagrammatically in FIG. 1.

The HIFU device bears the reference numeral 150 and is fitted with its ultrasound probe 160.

The parameterisation system 100 can receive data from the HIFU device, which data represents the area to be treated and the features of the probe, and in return can provide it with the parameters for insonifying the area in question.

The parameterisation system essentially comprises a simulation module 140 which, for each shot, is used to estimate the intensity of the ultrasonic field in the area to be treated and to deduce therefrom the thermal dose applied at each point in this area.

The parameterisation system can advantageously be equipped with an imaging device 110, a user interface 130, and a graphical interface 120.

The practitioner can view the area to be treated on the display of the imaging device and plan the treatment in the form of a sequence of shots, with each shot being defined by an arrangement of the probe relative to the area to be treated (position and orientation of the probe relative thereto), a focal point, in other words a delay law for the pulses applied to the various elements of the probe, a pulse energy (power and duration, where applicable), or even an ultrasound frequency.

Alternatively, the shot sequence can have been previously defined by the practitioner using the HIFU device and the corresponding data transmitted to the parameterisation system. This can in particular be the case if a patient's previous treatment has been recorded in the HIFU device.

In any case, the area to be treated and the successive shots can be viewed on the display of the imaging device. This device could, for example, be that of a conventional ultrasonograph.

Using the user interface, the practitioner can define additional shots or delete programmed shots, modify the position and/or orientation of the probe, or adjust the power and/or duration or repetition frequency of the shots, etc. The sequence of shots can be displayed superimposed over the image of the area to be treated.

Once the nominal treatment parameters have been defined (probe positions and orientations, power and duration of the shots, ultrasound frequency, shot repetition frequency, etc.), the simulation module, as described below, computes the spatial distribution of the ultrasonic field at each shot in near real-time, and uses this to deduce the distribution of the thermal dose in the tissue.

This ability to simulate the effects of a shot sequence in near real-time is essential, as it enables treatment to be carried out on an outpatient basis.

The thermal dose can then be mapped on the display screen and which parts have been necrotised and which have been preserved can be deduced by comparison with a threshold. The practitioner can thus check whether the HIFU treatment plan is in line with the desired objective and, if so, validate the transfer of treatment parameters to the HIFU device.

The module 140 can itself compare the result of the simulation with the desired objective and iteratively modify the parameters of the HIFU treatment device to comply with the treatment plan. For example, the simulation module can adjust the position and/or orientation of the probe relative to the area to be treated, the power and/or the duration of the shots, the rate of the shots, etc.

In all cases, the conformity of the parameterisation of the treatment device is validated by the practitioner using the user interface before the parameters are transferred to the HIFU device.

Figure 2:
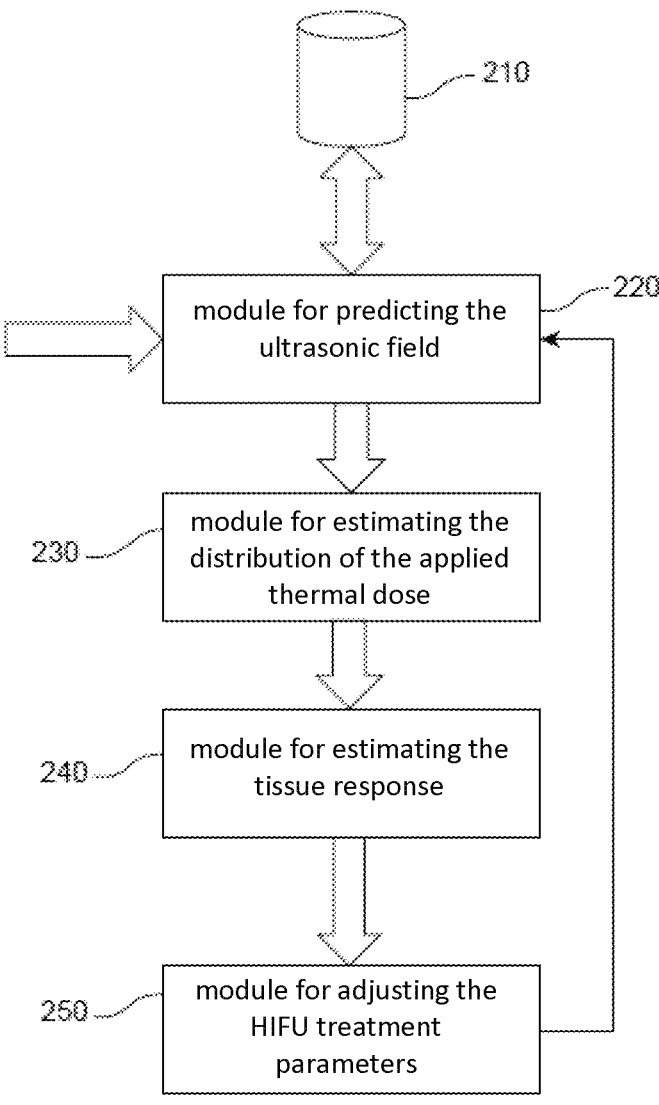
FIG. 2 diagrammatically shows the simulation module used in the parameterisation system shown in FIG. 1.

FIG. 2 diagrammatically shows the simulation module used in the parameterisation system shown in FIG. 1.

This simulation module uses a metamodel to predict the intensity of the ultrasonic field in the area to be treated, using a database 210. More specifically, the configuration of the area to be treated is modelled by breaking it down into different tissue regions, each tissue region being characterised by geometric and physiological parameters.

The configuration of the area to be treated can differ from one patient to another depending on the geometric parameters and physical parameters of the tissue regions that make it up. For example, tissue regions can be fat, blood, skin or the parenchyma of an organ.

The geometric parameters of the different tissue regions can be, for example, the thickness, radius of curvature and any other parameter that describes the shape or volume of such a region.

The physiological parameters of a tissue region can in particular include the tissue's acoustic attenuation coefficient, acoustic impedance, density, specific heat, thermal conductivity, and temperature, etc.

The database contains a map of the intensity of the acoustic field in the area to be treated for a plurality of possible configurations of this area and a plurality of treatment parameters. More specifically, for each configuration of said plurality, the database contains a map of the pressure field in the area to be treated.

For example, the database will contain a map of the pressure field for different thicknesses of skin, fat layer, size or values of geometric and/or physiological parameters of an organ. This map can be stored in the database for different treatment parameters and in particular different relative positions and orientations of the probe and of the area to be treated.

Each map is associated with an N-tuple of samples of these N geometric and physical parameters. For example, for a given inclination of the probe, a given thickness of skin, a given thickness of fat, and a value of acoustic attenuation in an organ, the database contains the pre-computed distribution of the intensity of the acoustic field in said area to be treated. For each of these configurations, this distribution will itself have been obtained by offline simulation (using the CIVA simulation platform for example). It is important to note that such a simulation requires significant computing resources and is thus incompatible with real-time restrictions.

The prediction module 220 extracts, from the database, the one or more ultrasonic field maps corresponding to the geometric and physical parameters closest to those defining the treatment protocol envisaged. The treatment protocol in particular includes the successive positions and orientations of the probe relative to the area to be treated.

These treatment parameters can be nominal parameters initially supplied by the HIFU device and/or those corrected by the practitioner using the imaging device 110 and the user interface 130.

The prediction module interpolates the ultrasonic field maps thus obtained to obtain a map corresponding to the geometric and physical parameters of the treatment.

This ultrasonic field map is obtained for each shot in the local reference frame of the probe and then transformed by changing the reference frame into a map in the reference frame of the area to be treated.

The map of the area to be treated is supplied to the module 230 for estimating the applied thermal dose. This module computes the temperature rise induced by the supply of ultrasonic energy at each point on a grid of points in the area to be treated.

The module 240 for estimating the tissue response then determines, at each point on the grid, whether or not the thermal dose applied, corresponding to the accumulation of thermal heating over time, will lead to tissue necrosis. To do this, this module can access the physiological parameters of the various tissues stored in the database 210. For example, for a given tissue, exceeding an applied thermal dose threshold will be one criterion for concluding that that tissue has been destroyed. However, if this threshold is not exceeded over the period in question, the tissue may be considered to have been preserved. Where appropriate, the criterion will be expressed as a probability of destruction based on statistics already obtained on the tissues in question.

A map of the necrotised regions or of the probability of tissue necrosis can then be superimposed over the image of the area to be treated on the display of the imaging device 110.

Advantageously, a module for adjusting the treatment parameters will use a cost function depending on the difference observed at each point on the regions to be destroyed. This cost function is minimised with the condition that the destruction criterion is not met in the regions to be preserved. Where appropriate, the different regions to be destroyed will be assigned weighting coefficients in the cost function according to the importance of their inclusion in the treatment.

The cost function can be expressed as a sum of unit functions.

These unit functions can in particular be associated with each shot. In such a case, each unit function can depend in particular on the position and orientation of the probe during the shot, on the power and duration of the pulses and on the focusing law applied (giving the position of the focal point) during this shot.

Unit functions can also be associated with tissue regions to be necrotised.

In particular, in some cases, a tissue region to be necrotised can be considered to comprise a plurality of sub-regions. In such a case, the cost function can comprise a sum of unit cost functions, with each unit cost function being associated with one of the sub-regions. It goes without saying that one or more shots can be used for each tissue region or sub-region to be necrotised. Regardless of whether a unit cost function is associated with a shot, with a tissue region or sub-region to be necrotised, or even with all of the regions to be necrotised, a unit cost function can take into account one or more objectives to be optimised. These objectives can in particular include:

a difference between a region or sub-region thereof estimated to have been necrotised by one or more shots and the corresponding region or sub-region thereof to be necrotised, a volume of healthy tissue necrotised after one or more shots, an overall (cumulative) duration of one or more shots, a number of positions of the probe for carrying out a set of shots, in particular all of the shots, and a rest period between two consecutive shots or a sum of such rest periods.

These objectives are taken into account in the cost function, in particular in order to improve patient comfort and/or optimise the availability of the treatment device.

The restricted cost function can be minimised in a conventional manner using Lagrange multipliers, for example by associating a Lagrange multiplier with each region to be preserved.

The cost function can be minimised using gradient descent, or even stochastic gradient descent when the number of shots is high, or genetic algorithms of the differential evolution type for example.

The new treatment parameters obtained are then injected into the prediction module 220 for a new prediction of the ultrasonic field.

At each iteration, the practitioner can view the map of necrotised regions and preserved areas and validate the transfer of treatment parameters to the HIFU device.

FIG. 3 diagrammatically shows a method for predicting the distribution of the ultrasonic field intensity used in FIG. 2.

The prediction method assumes that the area to be treated has already been modelled in step 310 into different tissue regions, each tissue region being characterised by a geometric and/or physiological parameter as described above.

It also assumes that the treatment protocol has been modelled in step 320 using treatment parameters such as the position and orientation of the probe relative to the area to be treated, as well as the power, duration, delay/phase law and frequency of the pulses applied to the various transducer elements of the probe for each shot. The shot sequence can be described by a probe trajectory relative to the area to be treated, which can be divided into slices where appropriate.

On the basis of the geometric and physiological parameters of the tissue regions, as well as the treatment parameters, the database is searched for the relevant configurations of these parameters, for example the configurations closest to or relating to values belonging to ranges around these parameters. The pre-computed ultrasonic field maps associated with these different configurations are then extracted from the database.

In step 340, the ultrasonic field intensity distribution in the area to be treated is estimated in the local reference frame of the probe by interpolating the field maps extracted from the database. This estimate is repeated for each shot in the treatment protocol.

Finally, in step 350, the reference frame is changed with each shot so as to obtain the distribution of the ultrasonic field in the reference frame of the area to be treated.

Figure 4:
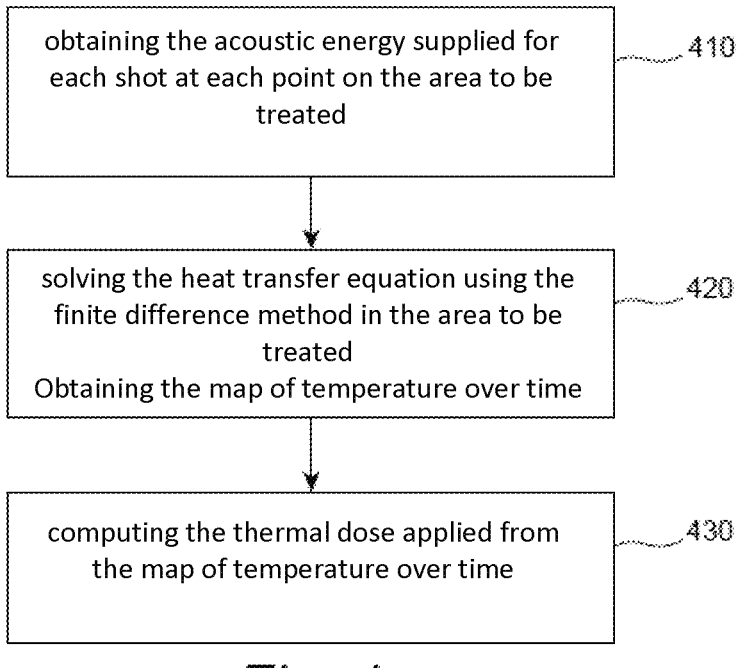
FIG. 4 diagrammatically shows a method for estimating the thermal dose applied in the area to be treated, and used in FIG. 2.

FIG. 4 diagrammatically shows a method for estimating the thermal dose applied in the area to be treated, and used in FIG. 2.

The area to be treated is spatially sampled by means of a grid of points.

For each shot, the acoustic energy delivered at each point on the grid is estimated in step 410, for each point on the grid, taking into account the power and duration of the shot and the attenuation along the propagation paths in the various tissue regions.

In step 420, the Bio Heat Transfer Equation (BHTE) is solved using an explicit finite difference method. A presentation of this solving method can be found in J. Chato's "Fundamentals of Bioheat Transfer"; Springer Berlin, Heidelberg, 1990.

The BHTE can be expressed as follows:

$$\rho . C \frac{\delta T_P}{\delta t} = \nabla . k \nabla T_P + \omega_b C_b (T_A - T_P) + Q_P$$

where $T_P$ is the temperature at the point P and at the time t, $T_A$ is the temperature of the arterial blood, $\rho$, C and k are respectively the density, the specific heat of the tissue and the thermal conductivity of the tissue, $C_b$ and $\omega_b$ are respectively the specific heat of the blood and the blood perfusion rate, and finally $Q_p$ is the density of the ultrasound energy absorbed at the point P.

The initial conditions are given by the body temperature and by the arterial blood temperature. Boundary conditions can also be set, such as the temperature of the gel or liquid between the probe and the patient's body, in order to facilitate acoustic impedance matching.

Solving the BHTE allows the change in temperature over time to be obtained at each point on the grid.

The thermal dose applied at each point on the grid is then estimated in step 430. The thermal dose can be conventionally expressed as the equivalent duration of exposure to a reference temperature, i.e. 43° C., as described in the article by P. Lele entitled "Thresholds and mechanisms of ultrasonic damage to "organized" animal tissues" published in Symposium of Biological Effects and Characterization of Ultrasound Sources, Rockville, MD: DHEW (Pub) FDA; 78-8048, pp. 224-239, 1977.

The equivalent exposure time to the reference temperature at the point P is given by:

$$d_{43}(P) = \int_{t_0}^{t_{end}} R^{(43 - T_{P(t)})} dt$$

where R=0.25 if $T_P$<43° C. and R=0.5 otherwise, $t_0$ and $t_{end}$ are respectively the start and end times of the HIFU treatment.

If the equivalent duration of exposure exceeds a predetermined threshold value, the tissue is considered to have been necrotised. Otherwise, it is considered to have been preserved.

Other criteria for tissue destruction, for example the duration of exposure to a temperature above a threshold temperature, can be envisaged by a person skilled in the art without leaving the scope of the present invention.

The system for parameterising the HIFU treatment device allows a treatment protocol to be simulated in near real-time and, where appropriate, allows the nominal parameters to be adjusted so as to meet an objective defined by the contours of the regions to be necrotised and those of the regions to be preserved in the area to be treated. The practitioner can intervene at any time in the iterative process and add restrictions or remove others. Once the treatment parameters have been validated, they are transferred in the HIFU device to launch the treatment.

The invention claimed is:

1. A method for parameterizing a HIFU treatment device equipped with an ultrasound probe for nectrotizing at least one tissue region of an area to be treated of a patient, said treatment comprising a plurality of ultrasound shots based on treatment parameters defining a position and an orientation of the ultrasound probe at each ultrasound shot relative to the area to be treated, the area to be treated being modelled by different tissue regions, including a tissue region to be necrotized and a tissue region to be preserved, each tissue region having geometric parameters and physiological parameters, said parameterizing method comprising:

estimating an ultrasonic field in the area to be treated with a metamodel using a database in which precomputed ultrasonic field maps are stored for different values of the geometric and physiological parameters of each tissue region of said area, the estimated ultrasonic field being obtained by interpolation of the precomputed ultrasonic field maps;

estimating a thermal dose to be applied at each point on a grid within the area to be treated from the estimated ultrasonic field in the area;

estimating a tissue response at each point on said grid to determine whether or not the estimated thermal dose to be applied leads to necrosis at the point, thus defining an estimated necrotized tissue region and an estimated preserved tissue region; and adjusting the treatment parameters in order to minimize a cost function that is dependent on a difference between the estimated necrotized tissue region and the tissue region to be necrotized, while satisfying a constraint that the region to be preserved lies within the estimated preserved tissue region, wherein the cost function includes a sum of a plurality of unit cost functions, each of said unit cost functions being associated with a shot of the ultrasound shots, with the tissue region to be necrotized, or with a sub-region of the tissue region to be necrotized, and/or being a function to minimize or maximize at least one objective chosen from among:

a difference between a region or sub-region thereof estimated to have been necrotized by one or more of the ultrasound shots and the corresponding region or sub-region thereof to be necrotized, a volume of healthy tissue necrotized after one or more of the ultrasound shots, an overall duration of one or more of the ultrasound shots, a number of positions of the ultrasound probe for performing a set of the ultrasound shots, or a rest period between two consecutive shots of the ultrasound shots or a sum of such rest periods; and wherein the method further comprises performing the treatment of the patient, including the plurality of ultrasound shots, according to the adjusted treatment parameters.

2. The method for parameterizing the HIFU treatment device according to claim 1, wherein said treatment parameters further comprise a duration and a repetition rate of the ultrasound shots.

3. The method for parameterizing the HIFU treatment device according to claim 1, wherein the ultrasound probe comprises a plurality of transducer elements, and said treatment parameters comprise a phase and/or a frequency and/or a power law to be applied to all of the transducer elements of the ultrasound probe.

4. The method for parameterizing the HIFU treatment device according to claim 1, wherein the physiological parameters of the tissue region include at least a density, a specific heat, a tissue thermal conductivity, a specific heat of blood, or a tissue blood perfusion rate.

5. The method for parameterizing the HIFU treatment device according to claim 1, wherein the step of estimating the ultrasonic field further comprises estimating the ultrasonic field in a local reference frame of the ultrasound probe by interpolating said pre-computed ultrasonic field maps, a distribution of the ultrasonic field in the area being deduced by changing the local reference frame.

6. The method for parameterizing the HIFU treatment device according to claim 1, wherein the step of estimating the thermal dose further comprises estimating the thermal dose by solving a heat transfer equation in the different tissue regions, taking into account an ultrasound energy absorbed at each point on the grid during each ultrasound shot of the plurality of ultrasound shots.

7. The method for parameterizing the HIFU treatment device according to claim 1, wherein a result of the treatment is simulated by computing, at each point on the grid, the thermal dose absorbed at that point in a form of an exposure time equivalent to a reference temperature, a tissue being considered necrotized at that point if that time exceeds a predetermined threshold value, and preserved otherwise.

8. The method for parameterizing the HIFU treatment device according to claim 7, wherein the cost function depends on a difference between an extent of the tissue region to be necrotized and an extent of the estimated necrotized tissue region.

9. The method for parameterizing the HIFU treatment device according to claim 1, wherein during the step of adjusting the treatment parameters, the treatment parameters are adjusted iteratively using a gradient descent algorithm, a stochastic gradient descent algorithm, or a genetic algorithm.

10. The method for parameterizing the HIFU treatment device according to claim 9, wherein, for at least one treatment parameter adjustment iteration, the estimated necrotized tissue region and/or the estimated preserved tissue region is/are displayed on a display, with the tissue region to be necrotized and/or the tissue region to be preserved overlaying an image of the area to be treated.

11. A system for parameterizing a HIFU treatment device equipped with an ultrasound probe for necrotizing at least one tissue region of an area to be treated of a patient, said treatment comprising a plurality of ultrasound shots based on treatment parameters defining a position and an orientation of the ultrasound probe at each ultrasound shot relative to the area to be treated, the area to be treated being modelled by different tissue regions, including a tissue region to be necrotized and a tissue region to be preserved, each tissue region having geometric and physiological parameters, said system comprising:

a module for estimating an ultrasonic field in the area to be treated with a metamodel, using a database in which precomputed ultrasonic field maps are stored for different values of the geometric and physiological parameters of each tissue region of said area, said estimation module estimating the ultrasonic field by interpolation of the precomputed ultrasonic field maps extracted from the database;

a module for estimating a thermal dose to be applied at each point on a grid within the area to be treated from the estimated ultrasonic field in the area;

a module for estimating a tissue response at each point on said grid to determine whether or not the estimated thermal dose to be applied leads to necrosis at the point, thus defining an estimated necrotized tissue region and an estimated preserved tissue region; and a module for adjusting the treatment parameters in order to minimize a cost function that is dependent on a difference between the estimated necrotized region and the tissue region to be necrotized, while satisfying a constraint that the region to be preserved lies within the estimated preserved tissue region; and the HIFU treatment device configured to perform the treatment of the patient, including the plurality of ultrasound shots, according to the adjusted treatment parameters, wherein the cost function includes a sum of a plurality of unit cost functions, each of said unit cost functions being associated with a shot of the ultrasound shots, with the tissue region to be necrotized, or with a sub-region of the tissue region to be necrotized, and/or being a function to minimize or maximize at least one objective chosen from among:

a difference between a region or sub-region thereof estimated to have been necrotized by one or more of the ultrasound shots and the corresponding region or sub-region thereof to be necrotized, a volume of healthy tissue necrotized after one or more of the ultrasound shots, an overall duration of one or more of the ultrasound shots, a number of positions of the ultrasound probe for performing a set of the ultrasound shots, or a rest period between two consecutive shots of the ultrasound shots or a sum of such rest periods.

12. The system for parameterizing the HIFU treatment device according to claim 11, wherein said treatment parameters further comprise a duration and a repetition rate of the ultrasound shots.

13. The system for parameterizing the HIFU treatment device according to claim 11, wherein the ultrasound probe comprises a plurality of transducer elements, and said treatment parameters comprise a phase and/or a frequency and/or a power law to be applied to all of the transducer elements.

* * * * *